US012427377B2

(12) United States Patent
Choi et al.

(10) Patent No.: US 12,427,377 B2
(45) Date of Patent: Sep. 30, 2025

(54) ELECTRONIC APPARATUS PROVIDING CONTENT-BASED CARE SERVICE AND CONTROLLING METHOD THEREOF

(71) Applicant: SAMSUNG ELECTRONICS CO., LTD., Suwon-si (KR)

(72) Inventors: Hyunmi Choi, Suwon-si (KR); Jungmi Park, Seongnam-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 210 days.

(21) Appl. No.: 18/196,724

(22) Filed: May 12, 2023

(65) Prior Publication Data

US 2023/0285807 A1    Sep. 14, 2023

Related U.S. Application Data

(63) Continuation of application No. PCT/KR2021/015211, filed on Oct. 27, 2021.

(30) Foreign Application Priority Data

Dec. 21, 2020 (KR) .................. 10-2020-0180222

(51) Int. Cl.
*A63B 24/00* (2006.01)
*A63B 71/06* (2006.01)
(Continued)

(52) U.S. Cl.
CPC ...... *A63B 24/0075* (2013.01); *A63B 71/0622* (2013.01); *G06V 20/50* (2022.01);
(Continued)

(58) Field of Classification Search
CPC .................................................. A63B 24/0075
See application file for complete search history.

(56) References Cited

U.S. PATENT DOCUMENTS

| 8,644,990 B2 | 2/2014 | Kim et al. |
| 9,177,457 B2 | 11/2015 | Shin et al. |

(Continued)

FOREIGN PATENT DOCUMENTS

| CN | 108040289 A | 5/2018 |
| JP | 2018-121697 A | 8/2018 |

(Continued)

OTHER PUBLICATIONS

Written Opinion (PCT/ISA/237) issued from the International Searching Authority on Jan. 26, 2022 to International Application No. PCT/KR2021/015211.

(Continued)

*Primary Examiner* — Travis R Hunnings
(74) *Attorney, Agent, or Firm* — Sughrue Mion, PLLC

(57) ABSTRACT

An electronic apparatus is provided. The electronic apparatus may include a display; a camera; a memory in which reference information associated with a content that provides information is stored; and a processor may be configured to obtain an image photographing a user through the camera while the content is provided through the display; obtain context information associated with the user based on the image; identify an execution status of the user associated with the information provided by the content by comparing the obtained context information and the reference information; and control an output state of the content based on the execution status of the user.

20 Claims, 17 Drawing Sheets

(51) Int. Cl.
  *G06V 20/50* (2022.01)
  *G06V 40/10* (2022.01)
  *G06V 40/20* (2022.01)
  *G16H 20/30* (2018.01)

(52) U.S. Cl.
  CPC .............. *G06V 40/10* (2022.01); *G06V 40/23* (2022.01); *G16H 20/30* (2018.01); *A63B 2024/0009* (2013.01); *A63B 2024/0068* (2013.01); *A63B 2214/00* (2020.08); *A63B 2220/807* (2013.01); *A63B 2230/625* (2013.01)

(56) References Cited

U.S. PATENT DOCUMENTS

| | | | |
|---|---|---|---|
| 9,189,613 B1 * | 11/2015 | Tuthill | G06Q 20/40 |
| 9,452,525 B2 | 9/2016 | Ziegler et al. | |
| 10,500,716 B2 | 12/2019 | Wei et al. | |
| 10,898,755 B2 | 1/2021 | Kang | |
| 11,074,826 B2 | 7/2021 | Wrigg et al. | |
| 2012/0000300 A1 * | 1/2012 | Sunagawa | A61B 5/4023 73/865.4 |
| 2015/0080183 A1 | 3/2015 | Alessandri et al. | |
| 2016/0216770 A1 | 7/2016 | Jang et al. | |
| 2019/0228672 A1 | 7/2019 | Wrigg et al. | |
| 2020/0105040 A1 * | 4/2020 | Chamdani | A63F 13/212 |
| 2020/0197746 A1 | 6/2020 | Kang | |
| 2020/0306587 A1 * | 10/2020 | Jabr | A63B 71/0622 |

FOREIGN PATENT DOCUMENTS

| | | |
|---|---|---|
| JP | 6881635 B2 | 6/2021 |
| KR | 10-1711488 B1 | 3/2017 |
| KR | 10-1886678 B1 | 8/2018 |
| KR | 10-2019-0038748 A | 4/2019 |
| KR | 10-1986327 B1 | 6/2019 |
| KR | 10-2000763 B1 | 7/2019 |
| KR | 10-2020-0072931 A | 6/2020 |
| KR | 10-2020-0092612 A | 8/2020 |
| KR | 10-2020-0129327 A | 11/2020 |
| KR | 10-2020-0133847 A | 12/2020 |

OTHER PUBLICATIONS

International Search Report (PCT/ISA/210) issued from the International Searching Authority on Jan. 26, 2022 to International Application No. PCT/KR2021/015211.

Communication dated Aug. 18, 2025 issued by the Korean Patent Office for Korean Patent Application No. 10-2020-0180222.

* cited by examiner

FIG. 6B

|   |   | E+C | | | | | |
|---|---|---|---|---|---|---|---|
|   |   | 2 | 3 | 4 | 5 | 6 | 7 |
| S | 1 | I1 | I1 | I2 | I3 | I3 | I3 |
|   | 2 | I1 | I2 | I2 | I3 | I3 | I3 |
|   | 3 | I2 | I3 | I3 | I4 | I4(I5, I6) | I4(I5, I6) |
|   | 4 | I3 | I3 | I3 | I4 | I4(I5, I6) | I4(I5, I6) |

601, 602, 603, 604, 605

ELECTRONIC APPARATUS PROVIDING CONTENT-BASED CARE SERVICE AND CONTROLLING METHOD THEREOF

CROSS REFERENCES TO RELATED APPLICATIONS

The present application is a bypass continuation of International Application No. PCT/KR2021/015211, filed on Oct. 27, 2021, in the Korean Intellectual Property Office, which claims priority from Korean Patent Application No. 10-2020-0180222, filed on Dec. 21, 2020, in the Korean Intellectual Property Office, the disclosures of which are incorporated herein in their entireties.

FIELD

This disclosure relates to an electronic apparatus that provides a care service related to a content for providing information and a controlling method thereof.

BACKGROUND

Recently, as platforms based on User Generated Content (UGC) such as YouTube have become popular, content that can satisfy the needs of various users are being produced and distributed. Accordingly, robots that can provide such content to users are being actively developed. However, existing robots only perform or provide unidirectional content to users, and have difficulties in providing satisfactory services because they do not reflect changes in the characteristics and circumstances of the users that receive the content. Therefore, there has been a continuous demand for a method of providing user-friendly care services through interaction with users in the process of providing content.

SUMMARY

The present disclosure relates to an electronic apparatus that provides a user-friendly care service through an interaction with the user in the process of providing content and a controlling method thereof.

An electronic apparatus according to an embodiment may include a display; a camera; a memory in which reference information associated with a content that provides information is stored; and a processor may be configured to obtain an image photographing a user through the camera while the content is provided through the display; obtain context information associated with the user based on the image; identify an execution status of the user associated with the information provided by the content by comparing the obtained context information and the reference information; and control an output state of the content based on the execution status of the user.

The content may include sub information corresponding to each of a plurality of steps, and the processor may be configured to, while sub information corresponding to one step from among the plurality steps is provided through the display, identify the user's execution status regarding the one step by comparing the obtained user's context information and reference information corresponding to the sub information, and control an output state of the content related to the one step based on the user's execution status.

The memory may store information regarding an output type of content for each execution level of the user, and the processor may be configured to identify an execution level corresponding to the user's execution status, identify information regarding an output type of a content corresponding to the identified execution level among information stored in the memory, and control an output state of the content based on the identified output type.

The output type of the content may include at least one of still image output, repeated output of sub information corresponding to a specific step, output speed adjustment, or enlarged output of the content.

The apparatus may further include a driving unit, and the processor may be configured to obtain the user's posture information based on the image obtained while a content that provides health information including an exercise posture is provided through the display, identify the user's execution status regarding the exercise posture by comparing the obtained posture information and posture information included in the reference information, and control the driving unit to provide a different feedback for guiding the user's posture based on the user's execution status.

The electronic apparatus may be implemented as a robot that provides a healthcare service, and the robot may perform an operation of correcting the user's posture or provides guide information for guiding the user's posture so that the user executes an exercise posture provided by the content based on the user's execution status.

The processor may be configured to identify the user's execution level based on at least one of a degree of correspondence between the obtained posture information and posture information included in the reference information, a frequency of discrepancy between the obtained posture information and posture information included in the reference information, or a complexity of the exercise posture, and provide a feedback corresponding to the identified execution level.

The processor may be configured to obtain the user's status information based on the image obtained while a content that provides task information including a plurality of steps is provided through the display, identify the user's execution status regarding each of the plurality of steps by comparing the obtained status information and status information included in the reference information, and control the display to provide guide information corresponding to a step requiring a feedback from among the plurality of steps based on the user's execution status.

The processor may be configured to obtain the user's first status information by inputting the image to a first neural network model, obtain the user's second status information by inputting the user's voice to a second neural network model, and control the display to provide guide information corresponding to a step requiring a feedback from among the plurality of steps based on the identified execution status, the first status information and the second status information.

The apparatus may further include a speaker, and the processor may be configured to, based on an image of the user not being obtained while information regarding one step from among the plurality of steps is provided, control the speaker to output guide information related to the task information.

A controlling method of an electronic apparatus according to an embodiment may include obtaining an image photographing a user through a camera while a content that provides information is displayed; obtaining context information associated with the user based on the image; identifying an execution status of the user associated with the information provided by the content by comparing the obtained context information and the reference information associated with the content; and controlling an output state of the content based on the execution status of the user.

The content may include sub information corresponding to each of a plurality of steps, the identifying the user's execution status may include, while sub information corresponding to one step from among the plurality steps is provided through the display, identifying the user's execution status regarding the one step by comparing the obtained user's context information and reference information corresponding to the sub information, and the controlling an output state of the content may include controlling an output state of the content related to the one step based on the user's execution status.

The identifying the user's execution status may include identifying an execution level corresponding to the user's execution status, and the controlling an output state of the content may include identifying information regarding an output type of content corresponding to the identified execution level and controlling an output state of the content based on the identified output type.

The output type of the content may include at least one of still image output, repeated output of sub information corresponding to a specific step, output speed adjustment, or enlarged output of the content.

The obtaining context information related to the user may include obtaining the user's posture information based on the image obtained while a content that provides health information including an exercise posture is provided through the display, and the identifying the user's execution status may include identifying the user's execution status regarding the exercise posture by comparing the obtained posture information and posture information included in the reference information and providing a different feedback for guiding the user's posture based on the user's execution status.

According to various embodiments, a satisfactory care service may be provided to users who have different levels of understanding or different execution statuses regarding information provided through content.

BRIEF DESCRIPTION OF DRAWINGS

FIGS. 6A and 6B are exemplary views illustrating identifying an execution level corresponding to a user's execution status according to an embodiment;

DETAILED DESCRIPTION

Figure 1:
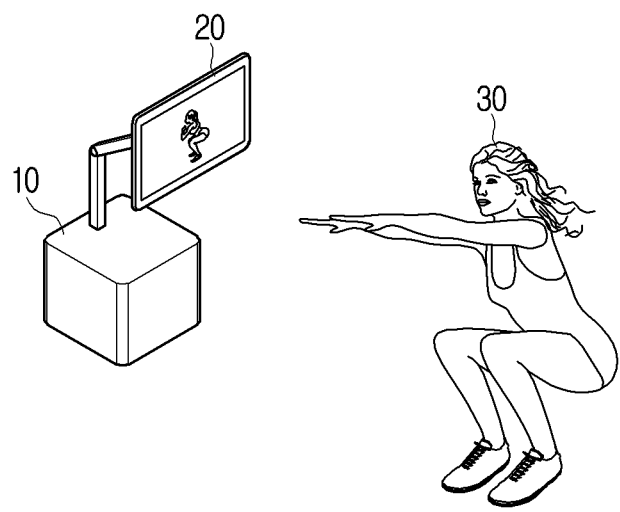
FIG. 1 is an exemplary view illustrating a content providing method regarding a user of an electronic apparatus.

Hereinafter, the present disclosure will be described with reference to the accompanying drawings.

The terms used in the example embodiments of the disclosure are general terms which are widely used now and selected considering the functions of the disclosure. However, the terms may vary depending on the intention of a person skilled in the art, a precedent, or the advent of new technology. In addition, in a specified case, the term may be arbitrarily selected. In this case, the meaning of the term will be explained in the corresponding description. Therefore, terms used in the disclosure may be defined based on a meaning of the terms and contents described in the disclosure, not simply based on names of the terms.

As used herein, the expression "have", "may have", "include", or "may include" refers to the existence of a corresponding feature (e.g., numeral, function, operation, or constituent element such as component), and does not exclude one or more additional features.

The expression of "at least one of A and/or B" is to be understood as indicating any one of "A" or "B" or "A and B".

The expression "a first", "a second", "the first", or "the second" used in various example embodiments of the disclosure may modify various components regardless of their order and/or the importance but does not limit the corresponding components.

When it is mentioned that any component (for example, a first component) is (operatively or communicatively) coupled to or is connected to another component (for example, a second component), it is to be understood that any component is directly coupled to another component or may be coupled to another component through the other component (for example, a third component). On the other hand, when it is mentioned that any component (for example, a first component) is "directly coupled" or "directly connected" to another component (for example, a second component), it is to be understood that the other component (for example, a third component) is not present between any component and another component.

A singular expression includes a plural expression as long as they are clearly distinguished in the context. In the application, it should be understood that the terms such as "comprising", "including" are intended to express that features, numbers, steps, operations, constituent elements, part, or combinations thereof described in the specification are present and do not exclude existence or additions of one or more other features, numbers, steps, operations, constituent elements, part, or combinations thereof.

In the disclosure, the term "module" or "unit" performs at least one function or operation, and may be embodied as hardware, software, or a combination thereof. A plurality of "modules" or a plurality of "units" may be integrated into at least one module to form at least one processor (not shown), except a "module" or "unit" which needs be embodied as particular hardware.

In the disclosure, the term "user" may refer to a person that uses an electronic apparatus. Hereinafter, an embodiment of the present disclosure will be described in greater detail with reference to the accompanying drawings.

FIG. 1 is a view provided to explain a content providing method regarding a user of an electronic apparatus.

Referring to FIG. 1, an electronic apparatus 10 may provide a content 20 that provides information to a user 30. Here, the content 20 may be a health-related content that describes a squat action.

The user 30 may follow a specific action based on information provided through the content 20 provided by the electronic apparatus 10. The action of the user 30 according to an embodiment may be an action of following a squat action included a health-related content.

The action of the user 30 according to another embodiment may be an action of following an origami action included in a kids-related content or an action of following an action of preparing ingredients included in a cooking-related content.

Meanwhile, the user 30 may only accept and understand information provided by the content 20, but may not following an action included in the content 20. The term 'execution status' used in the specification refers to a status related to information regarding whether the user understands information included in the content provided by the electronic apparatus or information regarding whether the user accurately follows a specific action based on information included in the content.

A plurality of users receiving the content 20 through the electronic apparatus 10 may have different abilities to perform the above-described action according to individual body characteristics and understanding of fields related to information provided through the content.

Specifically, a user with inflexible lower body may have difficulty in following a squat action, a color-weakened user may not be able to follow an origami action quickly, and a user who is not skilled in cutting may have difficulty in accurately following an action of preparing ingredients.

Therefore, in executing an action included in the content, each of the plurality of users who are provided with the content has different execution status. Nevertheless, existing electronic apparatuses have a problem in that they cannot provide a satisfactory service to users because they do not consider the execution status of the users.

Accordingly, hereinafter, various embodiments in which an electronic apparatus may provide a care service considering a user's execution status through an interaction with the user will be described in greater detail. In the present specification, the expression that an electronic apparatus 'provides an interaction' to a user and the expression that an electronic apparatus 'provides a feedback' are used interchangeably based on the premise that the two expressions have the same meaning.

Figure 2:
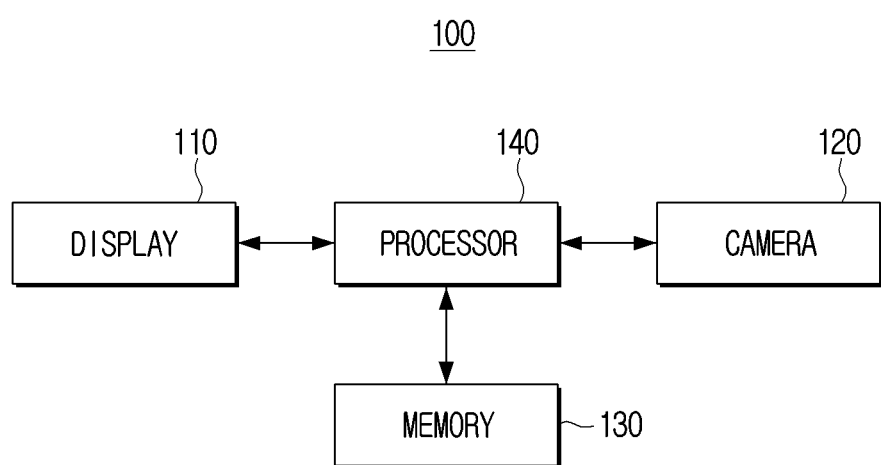
FIG. 2 is a block diagram illustrating an exemplary configuration of an electronic apparatus according to an embodiment.

FIG. 2 is a block diagram provided to explain configuration of an electronic apparatus according to an embodiment.

Referring to FIG. 2, an electronic apparatus 100 according to an embodiment may include a display 110, a camera 120, a memory 130, and a processor 140.

The display 110 may be implemented as various types of displays such as Liquid Crystal Display (LCD), Organic Light Emitting Diodes (OLED) display, Quantum dot light-emitting diodes (QLED) display, Plasma Display Panel (PDP), etc. The display 110 may include a driving circuit, a backlight unit, and the like, which may be implemented in the form such as an a-si thin film transistor (TFT), low temperature poly silicon (LTPS) TFT, or an organic TFT (OTFT). Meanwhile, the display 110 may be implemented as a flexible display, a 3D display and the like.

The camera 120 may obtain an image by capturing an area within a Field of View (FoV) of the camera.

The camera 120 may include a lens that focuses visible light or a signal reflected by an object, for example, a user, to an image sensor and an image sensor capable of detecting the visible light or the signal. Here, the image sensor may include a 2D pixel array that is divided into a plurality of pixels.

In addition, the camera 120 according to an embodiment may be implemented as a depth camera operating in a Time-Of-Flight (ToF) method.

The memory 130 may store data necessary for various embodiments of the present disclosure. The memory 130 may be implemented as a memory embedded in the electronic apparatus 100, or implemented in a memory form capable of being detachable from the electronic apparatus 100, based on a data storage purpose. For example, data for driving the electronic apparatus 100 may be stored in the memory embedded in the electronic apparatus 100, and data for an extension function of the electronic apparatus 100 may be stored in the memory capable of being detached from the electronic apparatus 100. Meanwhile, when implemented as the memory embedded in the electronic apparatus 100, the memory 130 may be implemented as at least one of a volatile memory (e.g., dynamic random access memory (DRAM), static RAM (SRAM), or synchronous dynamic RAM (SDRAM)), or a non-volatile memory (e.g., one time programmable read only memory (OTPROM), programmable ROM (PROM), erasable and programmable ROM (EPROM), electrically erasable and programmable ROM (EEPROM), mask ROM, flash ROM, flash memory (e.g., NAND flash, or NOR flash), hard drive, or solid state drive (SSD)). When implemented as the memory capable of being detached from the electronic apparatus 100, the memory 130 may be implemented in the form of a memory card (e.g., compact flash (CF), secure digital (SD), micro secure digital (Micro-SD), mini secure digital (Mini-SD), extreme digital (xD), or multi-media card (MMC)), or an external memory (e.g., USB memory) which may be connected to a universal serial bus (USB) port.

The memory 130 according to an embodiment may store reference information related to a content that provides information. Here, the reference information may be information corresponding to information included in the content that provides information.

The processor 140 controls the overall operations of the electronic apparatus 100. Specifically, the processor 140 may be connected to each component of the electronic apparatus 100 and control the overall operations of the electronic apparatus 100. For example, the processor 140 may be connected to the display 110, the camera 120 and the memory 130 and control the operations of the electronic apparatus 100.

According to an embodiment, the processor 140 may be referred to various names such as digital signal processor (DSP), microprocessor, central processing unit (CPU), micro controller unit (MCU), micro processing unit (MPU), neural processing unit (NPU), controller, application processor (AP), but it will be referred to as the processor 140 in the present specification.

The processor 140 may be implemented as System on Chip (SoC) or large scale integration (LSI), and it may also be implemented in the form of Field Programmable gate array (FPGA). In addition, the processor 140 may include a volatile memory such as SRAM.

The processor 140 according to an embodiment may obtain an image capturing a user through the camera 120 while a content is provided through the display 110.

The content according to an embodiment may be a content related to health, kids or cooking, but is not limited thereto. The processor 140 according to an embodiment may control the camera 120 to obtain an image including at least one of the user's front, side or back.

In addition, the processor 140 according to an embodiment may obtain context information related to the user based on the obtained image. The context information according to an embodiment may include information regarding the user's execution status corresponding to information provided through the content among information included in the obtained image.

Specifically, the context information according to an embodiment may include at least one of the posture information of the user who is receiving the content, the user's facial expression information or the user's voice information.

The processor 140 according to an embodiment may identify the user's execution status regarding information provided by the content by comparing the obtained context information and reference information stored in the memory 130.

In addition, the processor 140 according to an embodiment may control the output state of the content based on the identified user's execution status. Specifically, the processor 140 may change and provide the output type of the content that is being provided. The output type of content according to an embodiment may include at least one of still image output, repeated output of specific information included in the content, output speed adjustment, or enlarged output of the content.

The content according to an embodiment may consist of a plurality of steps including sub information. Specifically, when the content according to an embodiment is a health-related content, the content may consist of a plurality of steps including sub information corresponding to each action of exercise.

The processor 140 according to an embodiment may identify the user's execution status regarding one step by comparing the obtained user's context information and reference information corresponding to sub information while the sub information corresponding to one step from among a plurality of steps is provided through the display.

Specifically, when the content according to an embodiment is a health-related content, the processor 140 according to an embodiment may identify the user's execution status regarding a step corresponding to each action of exercise by comparing context information including the user's exercise posture information and reference information corresponding to sub information corresponding to each action.

The processor 140 according to an embodiment may control the output state of the content related to one step based on the identified user's execution status.

The processor 140 according to an embodiment may identify an execution level corresponding to the user's execution status. Here, the execution level according to an embodiment may be a level regarding how good the user's execution status is.

The processor 140 according to an embodiment may control the output state of the content based on information regarding the output type of content for each execution level of the user stored in the memory and the user's execution level.

When the content according to an embodiment consists of a plurality of steps including sub information, the processor 140 according to an embodiment may control the output state of the content so that sub information corresponding to a specific step included in the content is output repeatedly.

When the content according to an embodiment is a health-related content, the content may provide health information including an exercise posture. The processor 140 according to an embodiment may obtain the user's posture information based on the image obtained while the content is provided through the display 110.

In addition, the processor 140 according to an embodiment may identify the user's execution status regarding the exercise posture by comparing the obtained posture information and posture information included in reference information. The processor 140 may control a driving unit provided in the electronic apparatus so as to provide different feedbacks for guiding the user' posture based on the identified execution status. Specifically, the processor 140 according to an embodiment may control the driving unit to provide different feedbacks including at least one of driving of the electronic apparatus 100 or driving a mechanical part provided in the electronic apparatus 100.

Here, the processor 140 according to an embodiment may identify the user's execution level based on at least one of a degree of correspondence between the obtained posture information and posture information included in the reference information, a frequency of discrepancy between the obtained posture information and posture information included in the reference information, or complexity of the exercise posture.

The electronic apparatus 100 according to an embodiment may be implemented as a robot that provides a healthcare service, and the robot according to an embodiment may provide an operation of correcting the user's posture as a feedback so that the user executes an exercise posture provided by the content based on the user's execution status.

In addition, the robot may provide an operation of providing guide information for guiding the user's posture as a feedback. This will be described in detail with reference to FIGS. 7A and 7B.

The processor 140 according to an embodiment may obtain the user's status information based on the image obtained while the content that provides task information is provided through the display 110. Here, the task information according to an embodiment may be information including a plurality of steps which are combined based on priorities between steps.

Specifically, among step 1, step 2 and step 3 included in the task information according to an embodiment, step 2 may be a step initiated on the premise of completion of step 1, and step 3 may be a step initiated on the premise of completion of step 1 and step 2.

The processor 140 according to an embodiment may identify the user's execution status for each of the plurality of steps by comparing the obtained status information and status information included in the reference information, and control the display 110 to provide guide information corresponding to a step requiring a feedback from among the plurality of steps based on the user's execution status.

The processor 140 according to an embodiment may obtain the user's first status information by inputting the obtained image to a first neural network model, and obtain the user's second status information by inputting the user's voice to a second neural network model.

The electronic apparatus 100 according to an embodiment may further include a speaker, and when the user's image is not obtained while information regarding one of the plurality of steps is provided, the processor m140 according to an embodiment may control the speaker to output guide information related to task information.

Specifically, when the user's image is not obtained, the processor 140 according to an embodiment may identify that the user stops watching the content, and control the speaker to output a guide voice informing that the content has been stopped. Meanwhile, the processor 140 may control the speaker to output a guide voice requesting the user to concentrate on the content.

Figure 3:
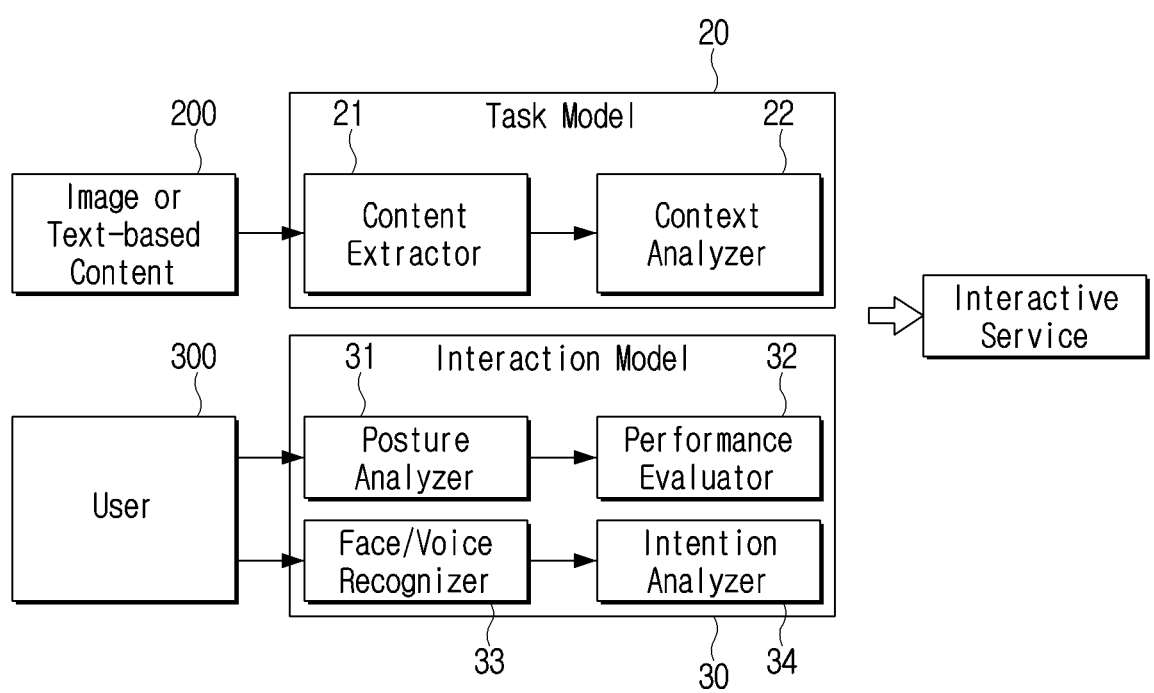
FIG. 3 is a block diagram illustrating an exemplary functional configuration of an electronic apparatus according to an embodiment.

FIG. 3 is a block diagram provided to explain functional configuration of an electronic apparatus according to an embodiment.

Each block illustrated in FIG. 3 may correspond to a plurality of modules related to functional configuration of the electronic apparatus 100. Here, the plurality of modules according to an embodiment may be a software module stored in a memory of the electronic apparatus 100 or a hardware module implemented as a circuit in the electronic apparatus 100. Alternatively, each of the plurality of modules may be implemented as a combination of software and hardware.

In the present disclosure, the functions of the electronic apparatus 100 will be described based on the assumption that functions performed by the plurality of modules are performed by the processor 140 which is one component of the electronic apparatus 100.

Referring to FIG. 3, the electronic apparatus 100 according to an embodiment may provide a user 300 with a service through a task model 20 and an interaction model 30. The task model 20 according to an embodiment may include a content extractor 21 and a context analyzer 22, and the interaction model 30 according to an embodiment may include a posture analyzer 31, an execution evaluator 32, a face/voice recognizer 33, and an intention analyzer 34.

A content 200 according to an embodiment may consist of a plurality of steps including sub information.

The content extractor 21 according to an embodiment may extract valid information from a video or text-based content 200. When the content 200 according to an embodiment is an image-based content, the content extractor 21 performs the function of extracting a content area according to a predetermined extraction rule from the image provided through the display 110.

The context analyzer 22 according to an embodiment may obtain a context based on information included in the content 200 that is provided through the extracted content area. Specifically, the context analyzer 22 may obtain a context based on a change in image, voice, subtitle, caption or the like included in the content 200.

The context analyzer 22 according to an embodiment may identify a plurality of steps consisting the content 200 based on the obtained context. When the content 200 according to an embodiment is a health-related content informing a squat action, the context analyzer 22 may identify a plurality of steps corresponding to 'taking a start posture', 'sitting down', 'standing up' and 'standing upright' based on information included in the content.

The task model 20 according to an embodiment may identify ideal forms of the identified plurality of steps based on reference information corresponding to the plurality of steps identified by the context analyzer 22.

The reference information according to an embodiment may be information generated based on the obtained context, but may be information stored in the memory 130 that is included in the electronic apparatus 100 based on specialized data. The reference information according to an embodiment may include main points and difficulties for steps as shown in Table 1 below.

TABLE 1

| Step | Main point | Complexity |
| --- | --- | --- |
| 1) Take a start posture | Leg width | Easy |
| 2) Sit down | Angle between thigh and shin Curvature of waist | Medium |
| 3) Stand up | Balance of left and right sides of body Direction of gaze | Hard |
| 4) Stand upright | Match rate with start posture | Easy |

With respect to a step corresponding to 'take a start posture', the task model 20 according to an embodiment may identify a case in which the difference between the leg width and the shoulder width is equal to or greater than a threshold value as an ideal form regarding the corresponding step. The interaction model 30 according to an embodiment may include a posture analyzer 31, an execution evaluator 32, a face/voice recognizer 33, and an intention analyzer 34. In addition, the interaction model 30 according to an embodiment may exchange information with the task model 20.

The posture analyzer 31 according to an embodiment analyzes a posture of the user 300. In FIG. 3, the term 'a posture analyzer' is used, but when information included in the content 200 is information related to a 'result' rather than a posture, the posture analyzer 31 may analyze a result made by the user 300 from the image obtained through the camera 120.

The posture analyzer 31 may obtain context information related to the user by analyzing a posture. Here, the context information related to the user may be information corresponding to the user's posture.

In addition, the posture analyzer 31 according to an embodiment may analyze a posture of the user 300 through Skeleton analysis which will be described in greater detail with reference to FIG. 5.

The execution evaluator 32 according to an embodiment may identify the user's execution status by comparing the user's posture information obtained through analysis in which sub information corresponding to one of a plurality of steps is provided and reference information corresponding to the sub information. When the content 200 according to an embodiment is a health-related content, the execution analyzer 32 may identify the user's execution status regarding the corresponding step by comparing the ideal form of 'take a start posture" which is one step included in the content and context information related to the user.

The face/voice recognizer 33 according to an embodiment may recognize the user's face and voice. Specifically, the face/voice recognizer 33 according to an embodiment may obtain the user's facial information based on an image capturing the user's face or obtain an utterance intention included in a voice by recognizing the user's voice.

The intention analyzer 34 according to an embodiment may identify a level of understanding of the user 300 regarding information provided by the content based on the obtained facial expression information or the utterance intention information.

When it is difficult to understand information provided by the content, the user 300 may make a specific facial expression or utter specific content. Specifically, the specific facial expression may be a frowning expression, and the specific content according to an embodiment may be content implying that information provided through the content 200 is difficult to understand.

Specifically, when the user's frowning expression is included in the image obtained while sub information corresponding to a specific step is provided, the intention analyzer 34 according to an embodiment may identify that the user's understanding for the corresponding step is not high.

Meanwhile, the intention analyzer 34 may obtain utterance intention information included in a voice by recognizing the user's voice, and identify the user's level of understanding based on the obtained utterance intention information.

The interaction model 30 according to an embodiment may determine an interaction to be provided to the user 300 based on information exchange with the task model 20.

Specifically, the interaction model 30 may provide different types of interactions based on the user's execution status or the user's level of understanding regarding information provided through the content 200.

The interaction model 30 according to an embodiment may determine an interaction to be provided to the user 300 based on not only the user's execution status and level of understanding but also factors unrelated to the user's characteristics such as complexity of individual steps constituting a content and specifications of electronic apparatuses.

The electronic apparatus 100 according to an embodiment based on functions performed by the above-described plurality of modules may provide an interaction appropriate for the user 300 in consideration of the user's execution status and understanding, improving the user's satisfaction for services.

Figure 4:
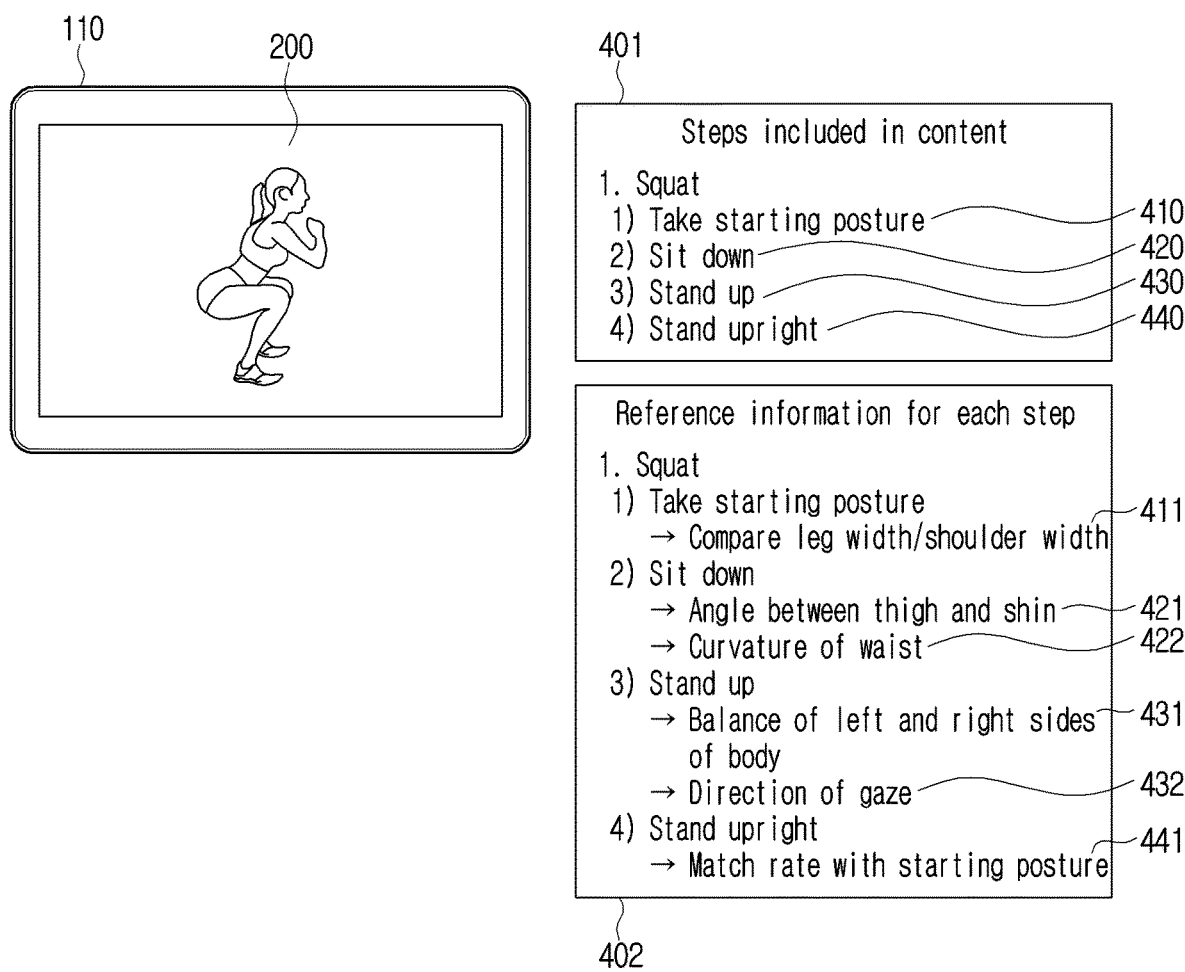
FIG. 4 is an exemplary view illustrating a step included in a content and reference information for each step.

FIG. 4 is a view provided to explain a step included in a content and reference information for each step.

Referring to FIG. 4, the content 200 may be provided on the display 110 provided in the electronic apparatus 100 according to an embodiment. Here, the content 200 according to an embodiment may be a health-related content that informs a squat action.

The processor 140 according to an embodiment may identify a plurality of steps included in a content 401. Specifically, the processor 140 may identify steps corresponding to 'take a start posture 410', 'sit down 420', 'stand up 430', and 'stand upright 440' constituting a squat action.

The processor 140 according to an embodiment may obtain reference information for each step 402. Here, the reference information for each step 402 according to an embodiment may be stored in the memory 130 included in the electronic apparatus 100.

Specifically, reference information corresponding to 'take a start posture 410' may be threshold value information 411 corresponding to a difference between a leg width and a shoulder width. In addition, reference information corresponding to 'sit down 420' may be information regarding an angle 421 between the thigh and shin and a waist curvature 422. Reference information corresponding to 'stand up 430' may be information regarding a balance of the left and right sides of the body 431 and a direction of gaze 432, and reference information corresponding to 'stand upright 440' may be information regarding a match rate with the start posture.

The ideal form corresponding to the 'sit down 420' step according to an embodiment may be a posture in which the angle between the thigh and shin is 90 degrees, and the curvature of waist is equal to or greater than 1(1/m).

Figure 5:
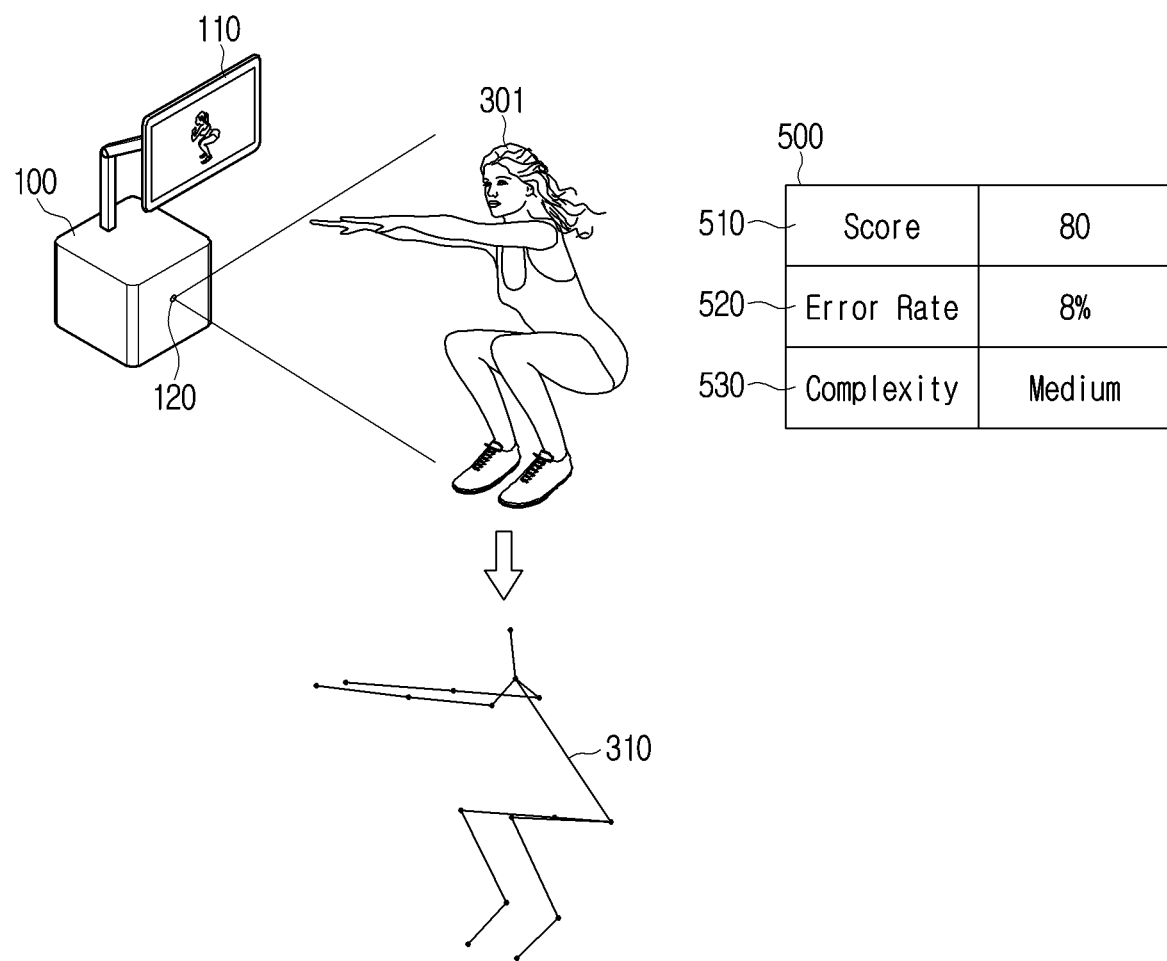
FIG. 5 is an exemplary method of identifying a user's execution status based on posture information according to an embodiment.

FIG. 5 is a view provided to explain a method of identifying a user's execution status based on posture information according to an embodiment.

The processor 140 according to an embodiment may identify the user's execution status for each step based on the identified reference information for each step 402 and the user's context information. In FIG. 5, it is assumed that the user's context information is the posture information of a user 301 who executes a squat action.

The processor 140 according to an embodiment may obtain posture information of the user 300 through skeleton analysis. The skeleton analysis is an analysis method for analyzing actions included in an image.

In order for the skeleton analysis, the camera 120 provided in the electronic apparatus 100 according to an embodiment may be implemented as a depth camera. Specifically, the processor 140 according to an embodiment may identify a point corresponding to a joint in the user's body included in an image obtained through a depth camera. In addition, the processor 140 may generate a skeleton model by connecting each point based on a positional relationship between points corresponding to joints. The skeleton analysis is a prior art in the field related to motion analysis and thus, further detailed descriptions will be omitted.

The processor 140 according to an embodiment may obtain a skeleton model 310 of the user through skeleton analysis regarding an image of the user 301 obtained through the camera 120. The processor 140 according to an embodiment may obtain the user's posture information based on the user's skeleton model 310.

The processor 140 according to an embodiment may identify the user's execution status for each step based on the user's posture information and reference information for each step 402.

Referring to FIG. 5, a user is executing an action corresponding to 'sit down 420' from among steps included in a content. The processor 140 according to an embodiment may identify the user's execution status based on the posture information of the user 301 who executes the 'sit down 420' action and reference information corresponding to the 'sit down 420' action.

Specifically, the processor 140 may identify the user's execution status corresponding to the 'sit down 420' based on whether the user has maintained the angle between the thigh and shin at a certain angle and whether the waist curvature is equal to or greater than a threshold curvature.

The processor 140 according to an embodiment may classify and identify the execution status according to various criteria. Specifically, the processor 140 according to an embodiment may identify the user's execution status 500 based on the user's execution score 510, error rate 520 and complexity of an action 530.

The execution score 510 according to an embodiment may be a numerical value identified based on how close the user's posture is to an ideal form regarding the corresponding step. The processor 140 according to an embodiment may identify that the user's execution score 510 is 80 points based on the degree of match between the user's posture and the ideal form corresponding to the 'sit down 420' step.

When the user repeats an action corresponding to the 'sit down 420' step multiple times, the processor 140 according to an embodiment may identify the average of the execution scores corresponding to each round as the final execution score 510 of the user.

The error rate 520 according to an embodiment means a probability rate that the user executes an action in which the match rate with an ideal form corresponding to a specific step is equal to or less than a threshold value. Specifically, when the user repeats an action corresponding to the 'sit down 420' step multiple times, the processor 140 according to an embodiment may identify that the rate at which the user executes an action indicating the match rate with an ideal form corresponding to the 'sit down 420' step being 70 percent or less is 8 percent.

The complexity 530 according to an embodiment means a level of complexity for the user to follow an ideal form for a step. Specifically, the level of complexity corresponding to the 'sit down 420' step may be 'medium.'

When the above-described error rate 520 is determined based on complexity corresponding to each step, the processor 140 may determine a threshold value which is a criterion. Specifically, when the level of complexity corresponding to a specific step is 'easy', the processor 140 may determine that the threshold value which is a criterion for determining the error rate 520 is 90 percent. Meanwhile, when the level of complexity is 'medium', the processor 140 may determine the threshold value as 80 percent, and when the level of complexity is 'hard', the processor 140 may determine the threshold value as 70 percent.

Figure 6A:
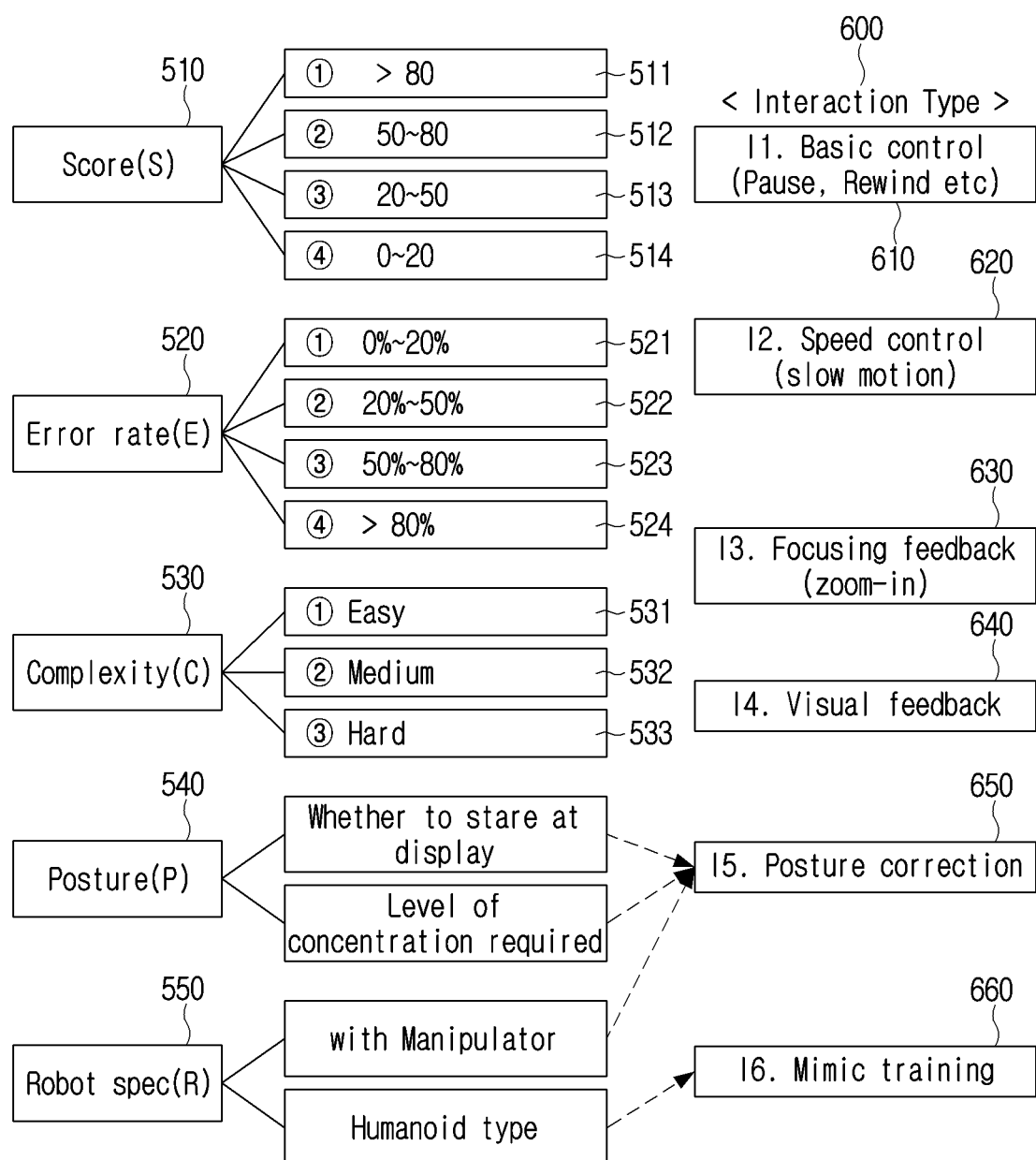

FIGS. 6A and 6B are views provided to explain an operation of identifying an execution level corresponding to a user's execution status by an electronic apparatus according to various criteria and various types of feedbacks provided by the electronic apparatus based on execution level the according to an embodiment.

Referring to FIG. 6A, the electronic apparatus 100 according to an embodiment may identify a user's execution level with reference to the execution score 510, the error rate 520 and the complexity 530.

The processor 140 according to an embodiment may identify an execution level corresponding to an execution status which is classified based on the numerical values of the execution score 510 and the error rate 520. Specifically, when the user's execution score exceeds 80 points (511), the processor 140 may identify the execution level corresponding to the user's execution status classified as the execution score 510 to be '1'.

Meanwhile, when the user's execution score is greater than 50 and equal to or less than 80 (512), the processor 140 may identify the execution level corresponding to the user's execution status classified as the execution score 510 to be '2'.

When the error rate is greater than 50 percent and equal to or less than 80 percent (523), the processor 140 according to an embodiment may identify the execution level corresponding to the user's execution status classified as the error rate 520 to be '3'.

Meanwhile, when the error rate exceeds 80 percent (524), the processor 140 according to an embodiment may identify the execution level corresponding to the user's execution status classified as the error rate 520 to be '4'.

When the level of complexity is easy (531), the processor 140 according to an embodiment may identify the user's execution status classified as the complexity 530 to be '1'. Since the case of the 'hard' complexity (533) requires more active interaction than the case of the 'easy' complexity (531), the processor 140 according to an embodiment may identify the execution level corresponding to the user's execution status classified as the complexity 530 to be high as the complexity increases.

Meanwhile, the electronic apparatus 100 according to an embodiment may classify execution statuses according to various criteria and then, provide various types of interactions 600 based on a plurality of execution levels obtained based thereon.

Specifically, interaction types according to an embodiment may include basic control 610, speed control 620, focusing feedback 630, visual feedback 640, posture correction 650, or mimic training 660.

The basic control 610 according to an embodiment may be an interaction type corresponding to still image output or repeated output of sub information corresponding to a specific step. Meanwhile, the visual feedback 640 according to an embodiment may be an interaction type in which the electronic apparatus 100 outputs an image capturing the user's posture through the camera 120 through the display 110, and the remaining interaction types will be described through the drawings later.

In FIGS. 6A and 6B, a plurality of interaction types described above are represented by symbols such as 'In (n is a natural number).' From I1 to I6, it means that the electronic apparatus 100 can provide active interaction to the user.

The processor 140 according to an embodiment may determine an interaction type to be provided based on the user's posture 540 as well as the execution level. Specifically, the processor 140 may determine whether to provide an interaction for posture correction 650 based on whether the user can gaze at the display and the level of concentration required to maintain the current posture of the user. This is because if the user cannot gaze at the display, there is a great need for posture correction using a separate driving unit (not shown) provided in the electronic apparatus 100, and if a lot of concentration is required for the user to maintain the current posture, performing posture correction in a physical method is more advantageous than controlling the output type of a content through the display.

In addition, when the electronic apparatus 100 is implemented as a robot, the processor 140 may determine whether to provide a mimic training 660 interaction based on a specification 550 of the robot. Specifically, when a robot according to an embodiment is implemented in a humanoid type, the robot may directly execute an ideal form corresponding to sub information provided through a content in order to guide a posture that the user intends to take for a specific step.

FIG. 6B illustrates various types of feedbacks provided by the electronic apparatus as a table based on an execution level. S on the vertical axis is a symbol representing an execution score, and E and C on the horizontal axis are symbols representing an error rate and complexity, respectively.

Specifically, when the sum of the execution level corresponding to the execution status classified as the error rate 520 and the execution level corresponding to the execution status classified as the complexity 530 is 3 and the execution level corresponding to the execution status classified as the execution score is 1 (601), the electronic apparatus according to an embodiment may provide an interaction of the basic control 610.

Meanwhile, when the sum of the execution level corresponding to the execution status classified as the error rate 520 and the execution level corresponding to the execution status classified as the complexity 530 is 4 and the execution level corresponding to the execution status classified as the execution score is 2 (602), the electronic apparatus according to an embodiment may provide an interaction of the speed control 620.

Meanwhile, when the sum of the execution level corresponding to the execution status classified as the error rate 520 and the execution level corresponding to the execution status classified as the complexity 530 is 6 and the execution level corresponding to the execution status classified as the execution score is 2 (603), the electronic apparatus according to an embodiment may provide an interaction of the focusing feedback 630.

Meanwhile, when the sum of the execution level corresponding to the execution status classified as the error rate 520 and the execution level corresponding to the execution status classified as the complexity 530 is 5 and the execution level corresponding to the execution status classified as the execution score is 4 (604), the electronic apparatus according to an embodiment may provide an interaction of the visual feedback 640.

Meanwhile, when the sum of the execution level corresponding to the execution status classified as the error rate 520 and the execution level corresponding to the execution status classified as the complexity 530 is 7 and the execution level corresponding to the execution status classified as the execution score is 4 (605), the electronic apparatus according to an embodiment may provide an interaction of the visual feedback 640. In this case, the processor 140 may provide an interaction of the posture correction 650 or the mimic training 660.

Figure 7A:
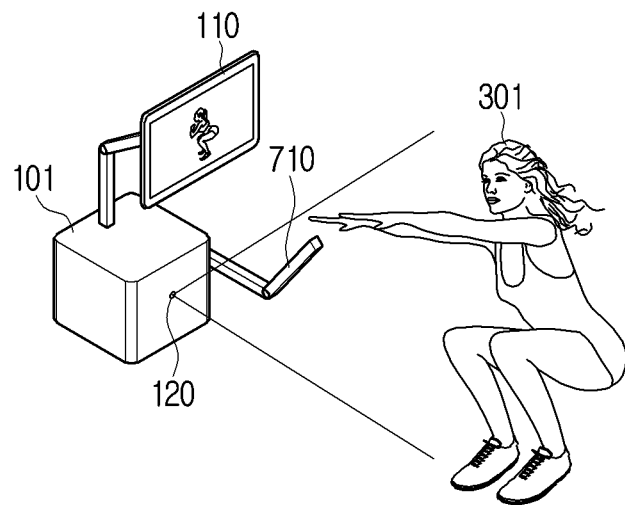
FIGS. 7A and 7B are views illustrating a posture correction operation and a mimic training operation of an electronic apparatus according to an embodiment.
Figure 7B:
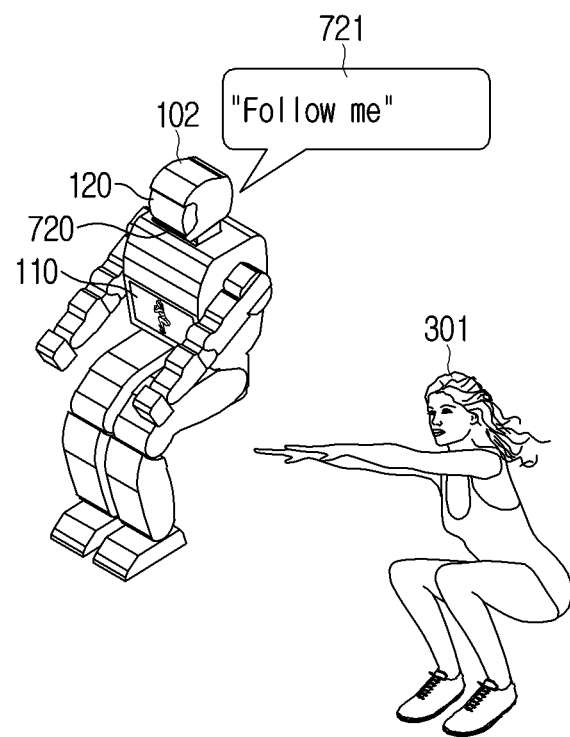

FIGS. 7A and 7B are views provided to explain a posture correction operation and a mimic training operation of an electronic apparatus according to an embodiment.

Referring to FIG. 7A, an electronic apparatus 101 according to an embodiment may include a driving unit 710. Unlike the description for FIG. 2, FIG. 7A illustrates that the driving unit 710 includes mechanical parts provided in the electronic apparatus 101, and not only the parts in the form of a robot shown therein but also the parts in the form of a wheel provided at the bottom of the electronic apparatus 100 and the parts in the form of an arm coupled to the real surface of the display 110 may also be included in the driving unit 710.

When it is identified that the user 301 requires a posture correction type of interaction, the electronic apparatus 101 may correct a wrong posture of the user 301 through the driving unit 710. The electronic apparatus 100 may touch the user 301 through the driving unit 710 in the process of providing the corresponding interaction.

In addition, the electronic apparatus 100 may move the position of the display 100 closer to the user 301 or adjust the angle of the display 100.

Referring to FIG. 7B, an electronic apparatus 102 according to an embodiment may be implemented as a humanoid type robot. Although not illustrated in FIG. 7B, the humanoid type robot 102 may include a driving unit including integrated configuration for driving the robot.

The robot 102 according to an embodiment may provide a mimic training type of interaction to a user by following an action corresponding to a specific step included in a content provided through the display 110.

In addition, the robot 102 according to an embodiment may include a speaker 720, and control the speaker 720 to output a voice of "please follow me" while providing a mimic training type of interaction to the user 301.

Figure 8A:
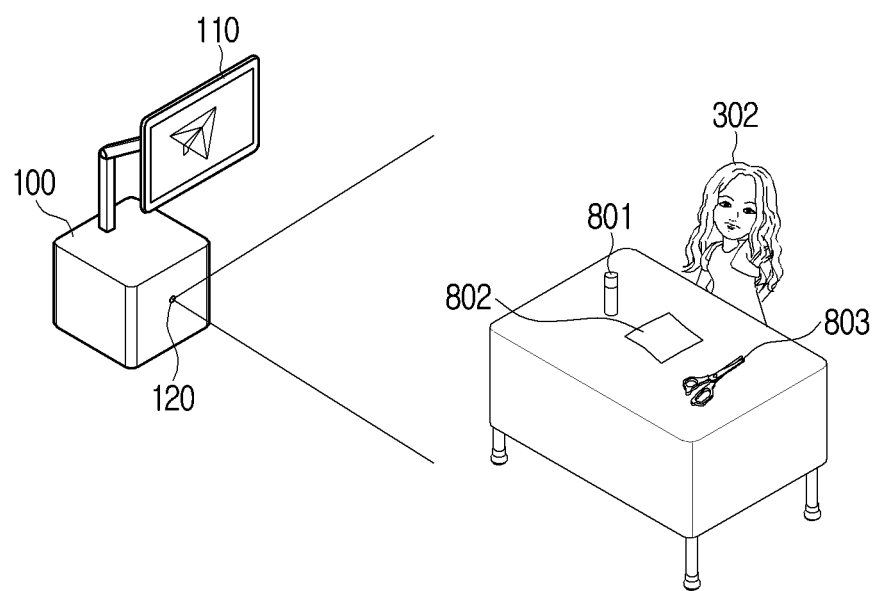
FIGS. 8A to 8C are views illustrating controlling an output state of a content by recognizing a user's facial expression by an electronic apparatus according to an embodiment.
Figure 8B:
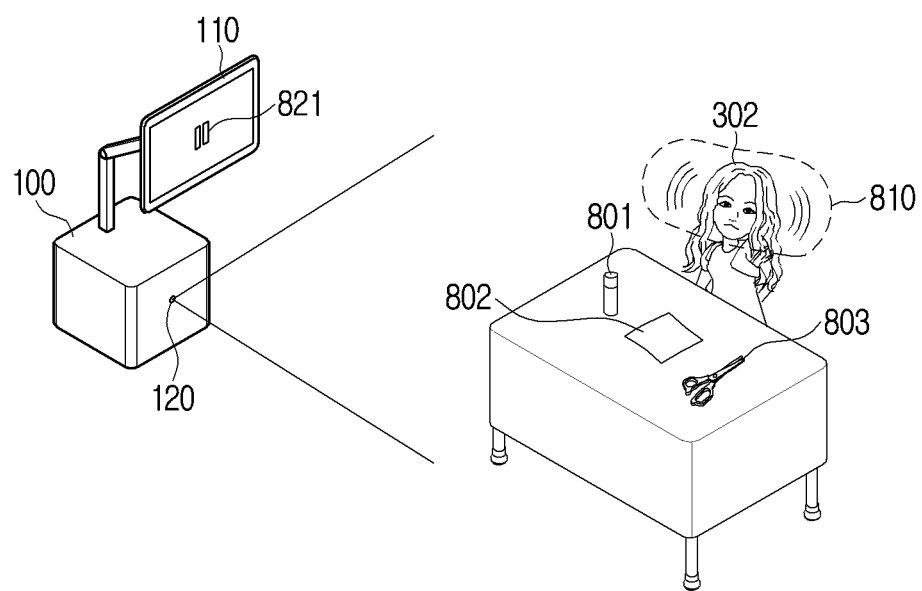
Figure 8C:
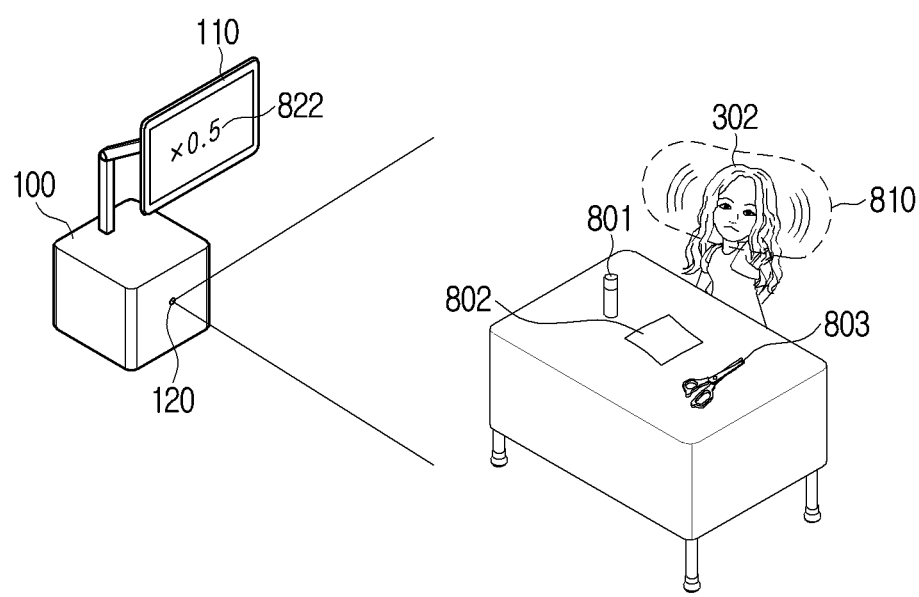

FIGS. 8A to 8C are views provided to explain an operation of controlling an output state of a content by recognizing a user's facial expression by an electronic apparatus according to an embodiment.

Referring to FIG. 8A, the electronic apparatus 100 according to an embodiment may provide an origami-related content that provides task information including a plurality of steps to a user 302. The processor 140 according to an embodiment may identify a plurality of steps included in an origami action.

The processor 140 according to an embodiment may identify 'a result' corresponding to each step as an ideal form for each step, and identify the execution status of the user 302 by comparing the result made by the user 302 and the ideal form.

The processor 140 according to an embodiment may provide an interaction regarding the user 302 based on the identified execution status. When the user does not make a result corresponding to a step, the processor 140 may repeatedly output sub information corresponding to the corresponding step. Meanwhile, the processor 140 may output sub information corresponding to the first step included in a content and continue to output sub information corresponding to subsequent steps.

In addition, when supplies 801, 802, 803 are not prepared, the processor 140 may provide a predetermined interaction prior to identifying the user's execution status.

The processor 140 according to an embodiment may identify the face of the user 302 based on an image obtained through the camera 120. The processor according to an embodiment may obtain the user's facial expression information based on the face image of the user.

The processor 140 according to an embodiment may obtain the user's facial expression information by inputting the face image to the first neural network model, and the first neural network model may be a model trained to receive a plurality of images and output an image including a frowning face.

The processor 140 according to an embodiment may identify that a user makes a frowning expression (810), and control the display 110 to provide guide information corresponding to a step requiring a feedback. Specifically, the processor 140 may control the display 110 to display guide information in which the output type of sub information corresponding to a step requiring a feedback has changed.

Specifically, guide information according to an embodiment may identify a step corresponding to sub information that is being provided at the moment when the user 302 makes a frowning expression from among steps included in an origami action, and provide a UI informing that sub information is provided again while providing sub information of the corresponding step again.

In addition, referring to FIG. 8B, the electronic apparatus 100 according to an embodiment may identify that a user makes a frowning expression (810), and immediately stop providing a content (821). Meanwhile, the processor 140 as shown in FIG. 8C may identify that a user makes a frowning expression (810), and immediately adjust the output speed of the content (822).

Figure 9A:
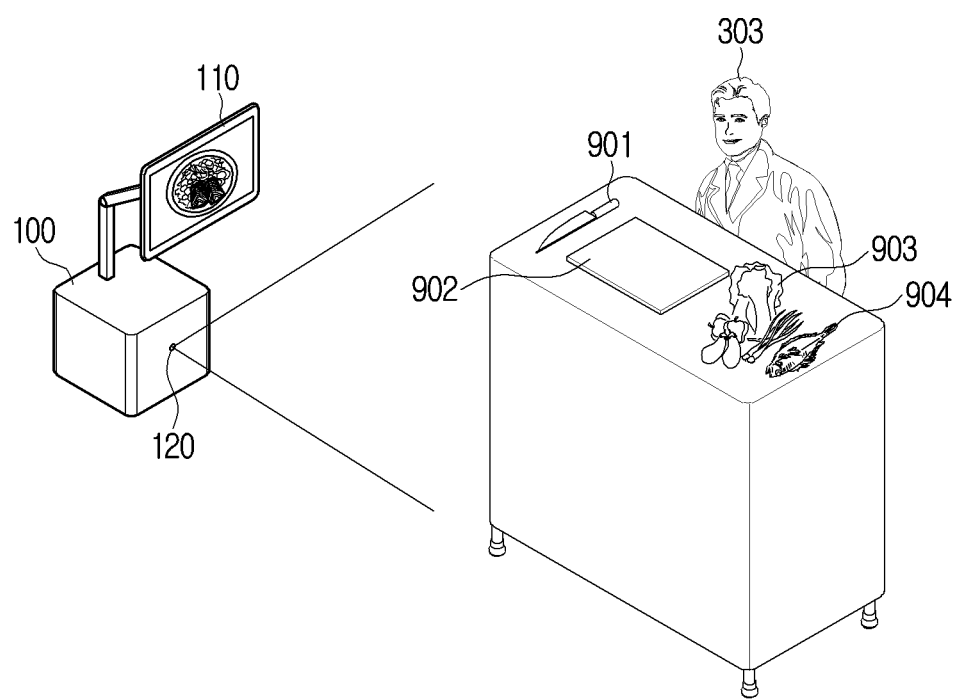
FIGS. 9A to 9C are views illustrating controlling an output state of a content by recognizing a user's voice by an electronic apparatus according to an embodiment.
Figure 9B:
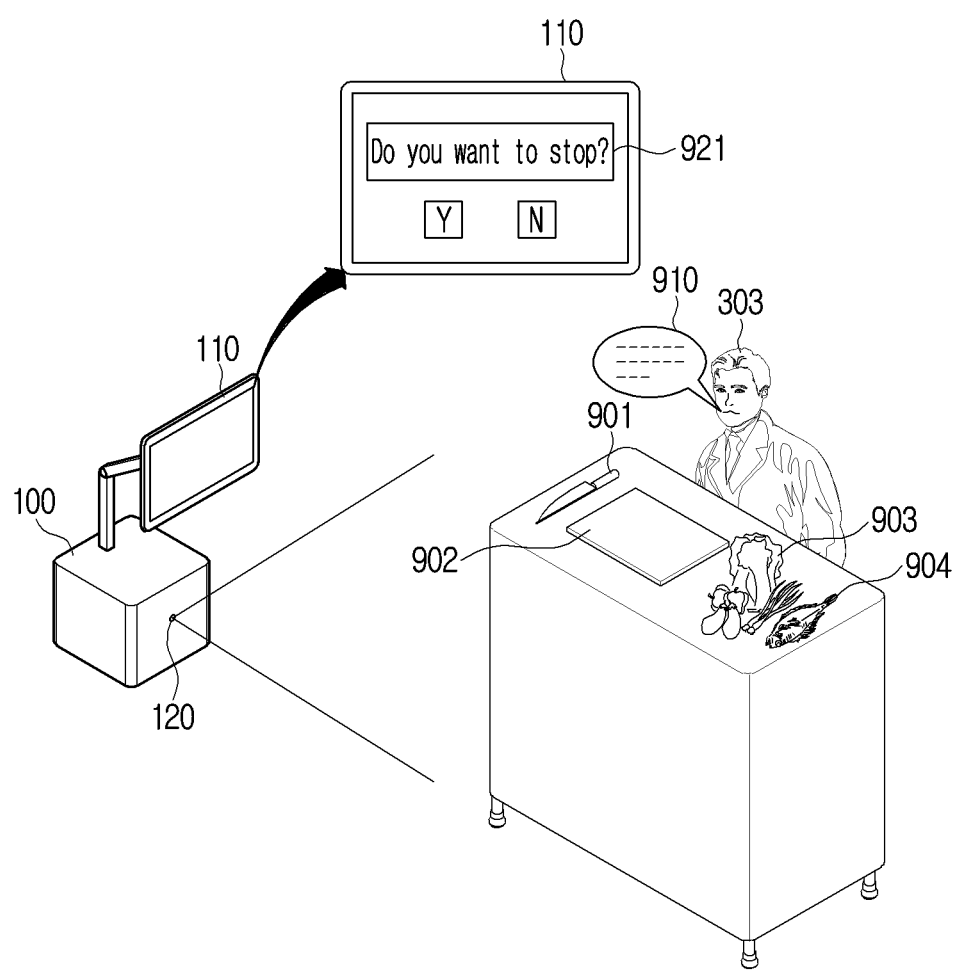
Figure 9C:
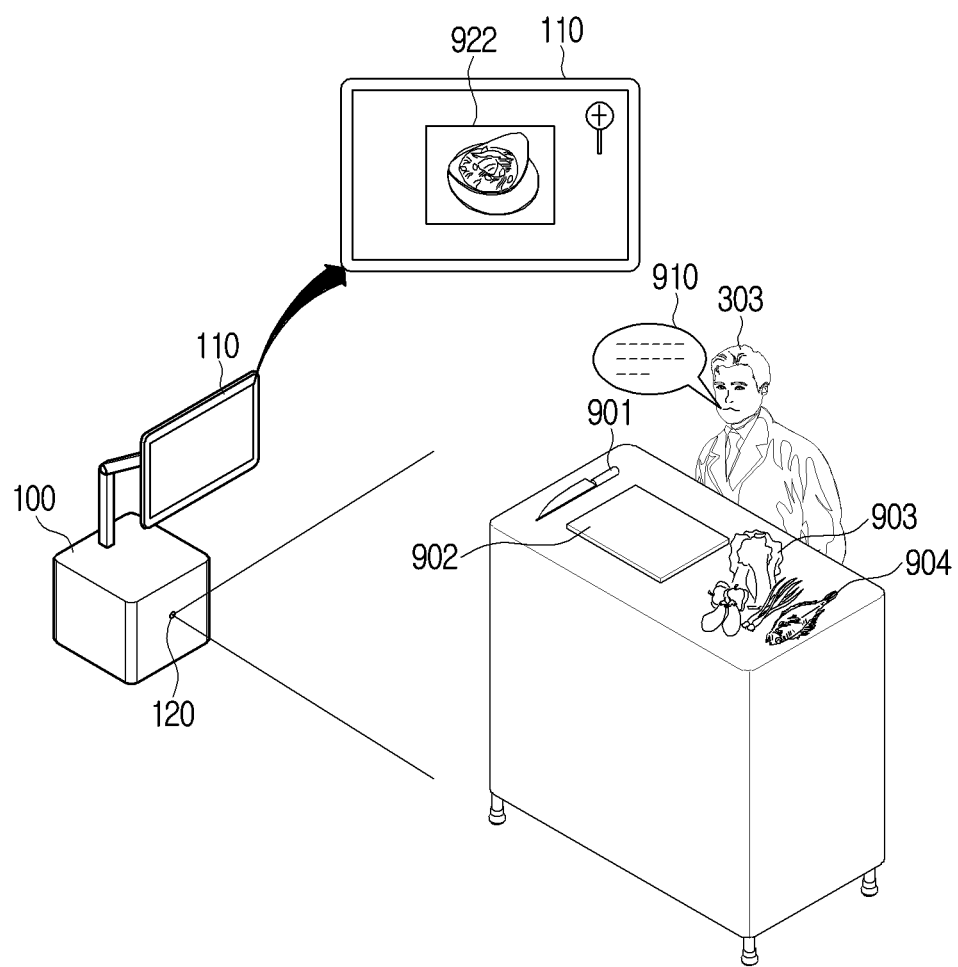

FIGS. 9A to 9C are views provided to explain an operation of controlling an output state of a content by recognizing a user's voice by an electronic apparatus according to an embodiment.

Referring to FIG. 9A, the electronic apparatus 100 according to an embodiment may provide a cooking-related content that provides task information including a plurality of steps to a user 303. The processor 140 according to an embodiment may identify a plurality of steps included in a cooking action.

The processor 140 according to an embodiment may identify 'a result' corresponding to each step as an ideal form for the step, and identify the execution status of the user 302 by comparing the result made by the user 303 with the ideal form.

The processor 140 according to an embodiment may provide an interaction regarding the user 303 based on the identified execution status. When the user does not make a result corresponding to the step, the processor 140 may repeatedly output sub information corresponding to the corresponding step. Meanwhile, the processor 140 may output sub information corresponding to the first step included in the content and continue to output sub information corresponding to subsequent steps.

In addition, when supplies 901, 902, 903, 904 are not prepared, the processor 140 may provide a predetermined interaction prior to identifying the user's execution status.

The processor 140 according to an embodiment may recognize the user's utterance. Specifically, the processor 140 may recognize the utterance based on the user's voice information obtained through a microphone (not illustrated) that is provided separately or recognize the utterance based on the user's mouth shape image obtained through the camera 120.

When the processor 140 according to an embodiment recognizes an utterance based on voice information, the processor 140 may obtain the user's utterance information by inputting the voice information to the second neural network model, and the second neural network model may be a model trained to receive a plurality of pieces of voice information and output a voice including an utterance describing an unpleasant mood.

The processor 140 according to an embodiment may identify an utterance describing the user's unpleasant mood and accordingly, control the display 110 to provide guide information corresponding to a step requiring a feedback. Specifically, the processor 140 may control the display 110 to display guide information in which the output type of sub information corresponding to a step requiring a feedback has changed.

Specifically, the guide information according to an embodiment may identify a step corresponding to sub information that is being provided at the moment when the user 303 utters from among steps included in a cooking action, and provide a UI informing that sub information is provided again while providing sub information of the corresponding step again.

In addition, referring to FIG. 9B, the electronic apparatus 100 according to an embodiment may identify the user's utterance 910, and display a UI 921 requesting an input regarding whether to stop providing a content. Meanwhile, as illustrated in FIG. 9C, the processor 140 may identify the user's utterance 910, and enlarge a specific part 922 of the screen provided through the content. This may be an interaction type corresponding to the focusing feedback 630 described in FIG. 6A.

Meanwhile, when it is identified that the user 303 is having a conversation with another person based on the user's voice received through a microphone, the processor 140 according to an embodiment may control the display 110 to stop providing the content.

As described in FIGS. 9A and 9B, the electronic apparatus 100 may provide various interactions based on the user's level of understanding regarding information included in the content.

Figure 10:
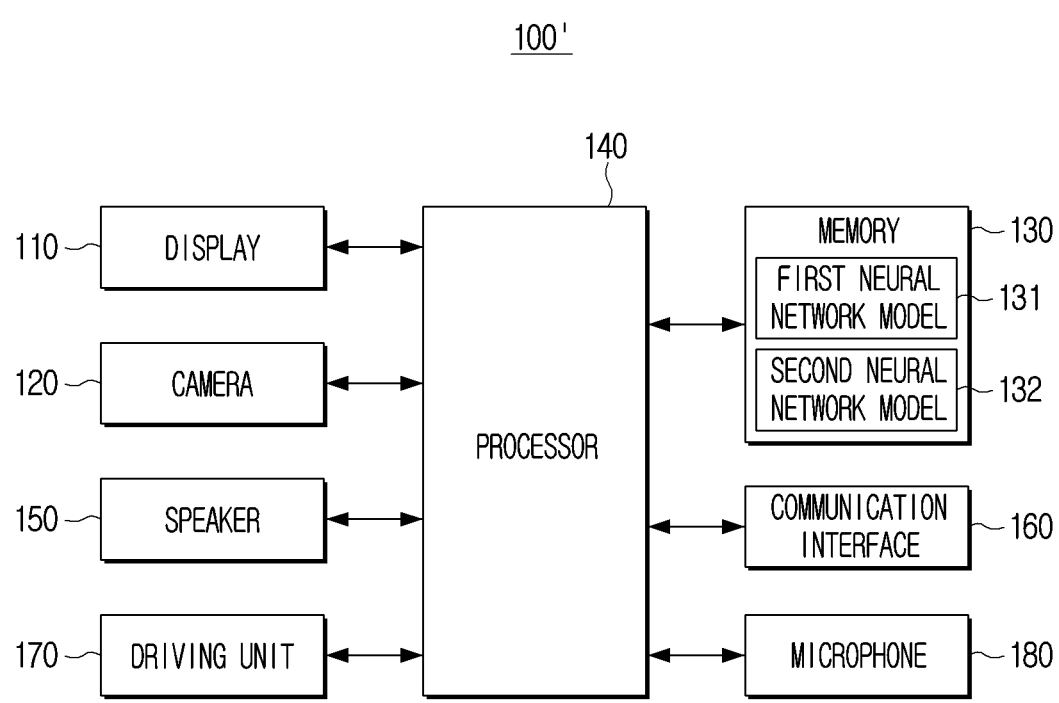
FIG. 10 is a functional block diagram illustrating the functional configuration of an electronic apparatus according to an embodiment.

FIG. 10 is a block diagram provided to specifically explain functional configuration of an electronic apparatus according to an embodiment.

Referring to FIG. 10, an electronic apparatus 100' includes the display 110, the camera 120, the memory 130, the processor 140, a speaker 150, a communication interface 160, a driving unit 170, and a microphone 180. Among components illustrated in FIG. 10, detailed descriptions regarding the components which overlap with those illustrated in FIG. 2 will be omitted.

The memory 130 according to an embodiment may store information regarding a first neural network model 131 and a second neural network model 132 including a plurality of layers. Here, storing information regarding a neural network model may mean storing various information related to the operations of a neural network model, for example, information regarding a plurality of layers included in the neural network model, information regarding a parameter (e.g., filter coefficients, biases, etc.) used in each of the plurality of layers, etc. For example, the memory 130 may store information regarding the first neural network model 131 trained to receive a plurality of images and output an image including a frowning facial expression and the store information regarding the second neural network model 132 trained to receive a plurality of pieces of voice information and output a voice including an utterance describing an unpleasant mood according to an embodiment.

The speaker 150 is a device that converts an electrical acoustic signal of the electronic apparatus 100 into sound waves. The speaker 150 may include a permanent magnet, a coil and a diaphragm, and may output sound by vibrating the diaphragm by electromagnetic interaction that occurs between the permanent magnet and the coil.

The communication interface 160 may input and output various types of data. For example, the communication interface 160 may transmit/receive various types of data to/from an external device (e.g., source device), an external storage medium (e.g., universal serial bus (USB) memory), an external server (e.g., web hard) or the like by using a communication method such as an access point (AP)-based wireless fidelity (Wi-Fi, i.e. wireless local area network (LAN)), a Bluetooth, a Zigbee, a wired/wireless local area network (LAN), a wide area network (WAN), Ethernet, an IEEE 1394, a high definition multimedia interface (HDMI), a USB, a mobile high-definition link (MHL), an audio engineering society/European broadcasting union (AES/EBU) communication, an optical communication or a coaxial communication.

When the electronic apparatus 100 provides a user with an interaction, the driving unit 170 may drive the electronic apparatus 100 under the control of the processor 140. Specifically, the driving unit 170 may move the position of the electronic apparatus 100 or drive mechanical parts included in the electronic apparatus 100. To this end, the driving unit 170 may include a power generating device that generates power (e.g., a gasoline engine, a diesel engine, a liquefied petroleum gas engine, an electric motor, etc. depending on the fuel (or energy source) used), a steering device (e.g., manual steering, hydraulics steering, electronic control power steering (EPS), etc.) for adjusting a driving direction, a driving device (e.g., wheels, propellers, etc.) for driving the electronic apparatus 100 according to power.

Here, the driving unit 170 may be provided in different forms based on the type in which the electronic apparatus 100 is implemented.

The microphone 180 is configured to receive a sound signal. Specifically, the microphone 180 is configuration that collectively refers to a device that receives a sound wave and generates a current of the same waveform. In the above drawings, it is described that a signal including a user's voice is received, but the microphone 180 according to an embodiment may receive various sound signals such as footsteps, breathing sounds, plosive sounds, etc.

Specifically, the processor 140 may identify whether a user who is executing a running action is exercising at an appropriate speed based on an interval of generation of footsteps received through the microphone 180. The processor 140 may identify whether the user's breathing is stable based on the breathing sound received through the microphone 180.

In addition, the processor 140 may identify that the user has been injured due to a cause such as a fall during exercise based on the plosive sound received through the microphone 180 and then, provide a corresponding interaction. Accordingly, the electronic apparatus 100 may recognize a situation more accurately when reliability of image information obtained through the camera 120 is low.

Figure 11:
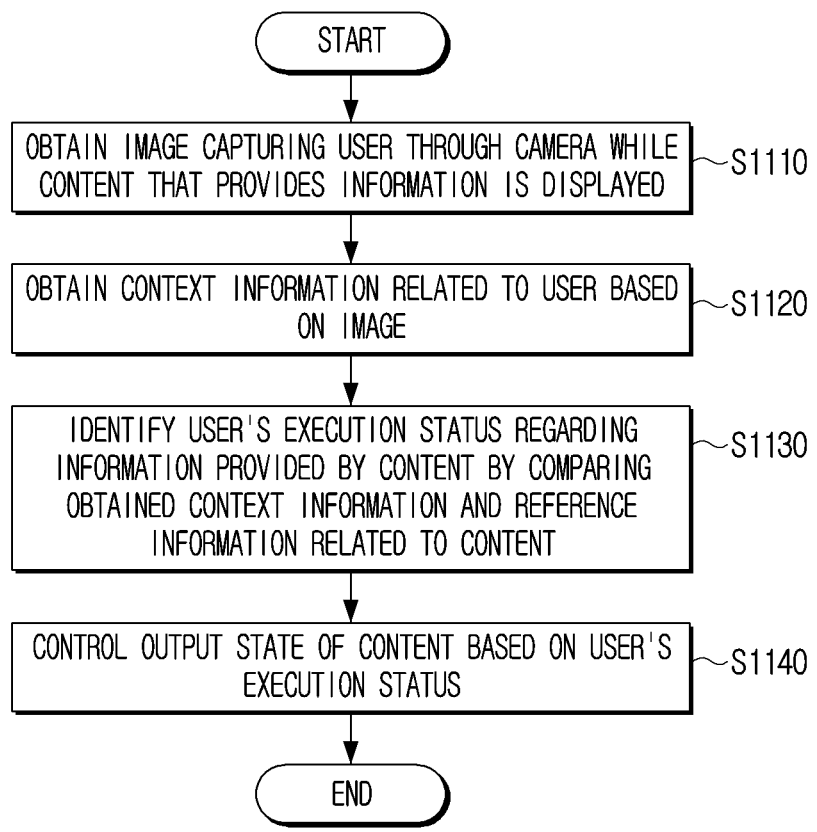
FIG. 11 is a flowchart illustrating a controlling method according to an embodiment.

FIG. 11 is a flowchart provided to explain a controlling method according to an embodiment.

A controlling method of an electronic apparatus according to an embodiment may include obtaining an image capturing a user through a camera while a content that provides information is being displayed (S1110). Subsequently, context information related to the user is obtained based on the image (S1120). By comparing the obtained context information and reference information related to the content, the user execution status regarding the information provided by the content is identified (S1130). Lastly, the output state of the content is controlled based on the user's execution status (S1140).

Here, the content includes sub information corresponding to each of a plurality of steps, and the identifying the user's execution status (S1130) may include identifying the user's execution status regarding one step by comparing the obtained user's context information and reference information corresponding to sub information while the sub information corresponding to one step from among a plurality of steps is provided through the display, and the controlling the output state of the content (S1140) may include controlling the output state of the content related to one step based on the user's execution status.

Here, the identifying the user's execution status (S1130) may include identifying an execution level corresponding to the user's execution status, and the controlling the output state of the content (S1140) may include identifying information regarding the output type of the content corresponding to the identified execution level and controlling the output state of the content based on the identified output type.

Here, the output type of the content may include at least one of still image output, repeated output of sub information corresponding to a specific step, output speed adjustment, or enlarged output of the content.

Meanwhile, the obtaining context information related to the user (S1120) may include obtaining the user's posture information based on an image obtained while a content that provides health information including an exercise posture is provided through the display, and the identifying the user's execution status (S1130) may include identifying the user's execution status regarding the exercise posture by comparing the obtained posture information and posture information included in reference information and providing a different feedback for guiding the user's posture based on the user's execution status.

Here, the electronic apparatus 100 is implemented as a robot that provides a healthcare service, and the providing a different feedback may include performing an operation of correcting the user's posture or guiding the user's posture so that the user can execute the exercise posture provided by the content.

In addition, the identifying the user's execution status (S1130) may further include identifying the user's execution level based on at least one of a frequency of discrepancy between the obtained posture information and posture information included in the reference information or a complexity of the exercise posture, and the providing a different feedback may include providing a feedback corresponding to the identified execution level.

Meanwhile, the obtaining context information related to the user (S1120) may include obtaining the user's status information based on the image obtained while the content that provides task information including a plurality of steps is provided through the display, and the identifying the user's execution status (S1130) may include identifying the user's execution status for each of the plurality of steps by comparing the obtained status information and status information included in reference information and providing guide information corresponding to a step requiring a feedback from among the plurality of steps based on the user's execution status.

Here, the obtaining the user's status information may include obtaining the user's first status information by inputting the image to the first neural network model and obtaining the user's second status information by inputting the image to the first neural network model and obtaining the user's second status information by inputting the user's voice to the second neural network model, and the providing guide information may include providing guide information corresponding to a step requiring a feedback from among a plurality of steps based on the first status information and the second status information.

In addition, when the user's image is not obtained while information regarding one of the plurality of steps is provided, guide information related to task information may be output.

Meanwhile, the methods according to various embodiments of the disclosure described above may be implemented in the form of an application that may be installed in an existing electronic apparatus.

In addition, the methods according to the diverse embodiments of the disclosure described above may be implemented only by software upgrade or hardware upgrade for the existing electronic apparatus.

In addition, various embodiments of the disclosure described above may be implemented by an embedded server included in an electronic apparatus or at least one external server.

Meanwhile, the various embodiments described above may be implemented in a computer or a computer-readable recording medium using software, hardware, or a combination of software and hardware. In some cases, the embodiments described in the present disclosure may be implemented by the processor 140 itself. According to a software implementation, the embodiments such as the procedures and functions described in the present disclosure may be implemented by separate software modules. Each of the software modules may perform one or more functions and operations described in the specification.

Meanwhile, a non-transitory computer-readable medium may store computer instructions for performing the processing operations of the electronic apparatus 100 according to the various embodiments of the present disclosure described above. The computer instructions stored in the non-transitory computer-readable medium may allow a specific device to perform the processing operations of the electronic apparatus 100 according to the various embodiments described above when the computer instructions are executed by a processor of the specific device.

The non-transitory computer-readable medium is not a medium that stores data therein for a while, such as a register, a cache, or a memory, and indicates a medium that semi-permanently stores data therein and is readable by the machine. A specific example of the non-transitory computer-readable medium may include a compact disk (CD), a digital versatile disk (DVD), a hard disk, a Blue-ray disk, a universal serial bus (USB), a memory card, a read-only memory (ROM), or the like.

Although the embodiments are shown and described in the present disclosure as above, the present disclosure is not limited to the above-mentioned specific embodiments, and may be variously modified by those skilled in the art to which the present disclosure pertains without departing from the gist of the present disclosure as claimed in the accompanying claims. These modifications should also be understood to fall within the scope and spirit of the present disclosure.

Although embodiments of the disclosure have been illustrated and described herein, the disclosure is not limited thereto, and various modifications may be made by those of ordinary skill in the art without departing from the gist of the disclosure defined in the appended claims and should not be understood separately from the technical idea or prospect of the disclosure.

What is claimed is:

1. An electronic apparatus comprising:
   a display;
   a camera;
   a memory in which reference information associated with a content that provides information is stored; and
   a processor configured to:
   obtain an image photographing a user through the camera while the content is provided through the display, the content comprising information corresponding to a plurality of steps;
   obtain context information associated with the user based on the image;
   identify an execution status of the user associated with the information provided by the content by comparing the obtained context information and the reference information; and
   control an output state of the content based on the execution status of the user; and
   control the display to provide guide information corresponding to a step, requiring a feedback, from among the plurality of steps based on the identified execution status.

2. The electronic apparatus as claimed in claim 1, wherein the content includes respective sub information corresponding to each of a plurality of steps; and
   wherein the processor is configured to;
   while the respective sub information corresponding to a first step from among the plurality of steps is provided through the display, identify the execution status of the user associated with the first step by comparing the obtained context information and reference information corresponding to the respective sub information; and
   control the output state of the content corresponding to the first step based on the execution status of the user.

3. The electronic apparatus as claimed in claim 2, wherein the memory stores a type of an output content for each execution level of the user; and
   wherein the processor is configured to:
   identify an execution level corresponding to the execution status of the user;
   identify information associated with the type of the output content corresponding to the identified execution level; and
   control the output state of the content based on the type of the output content.

4. The electronic apparatus as claimed in claim 3, wherein the type of the output content includes at least one of a still image output, repeated output of the respective sub information corresponding to a specific step, output speed adjustment, or enlarged output of contents.

5. The electronic apparatus as claimed in claim 1, further comprising:
   a driving unit,
   wherein the processor is configured to:
   obtain posture information of the user based on the image obtained while a content that provides health information including an exercise posture is provided through the display;
   identify the execution status of the user associated with the exercise posture by comparing the obtained posture information of the user and the posture information included in the reference information; and
   control the driving unit to provide a specific feedback for guiding the user's posture based on the execution status of the user.

6. The electronic apparatus as claimed in claim 5, wherein the electronic apparatus is implemented as a robot that provides a healthcare service; and
   wherein the robot performs an operation of correcting the user's posture or provides guide information for guiding the user's posture so that the user executes the exercise posture provided by the content based on the execution status of the user.

7. The electronic apparatus as claimed in claim 5, wherein the processor is configured to identify an execution level of the user based on at least one of a degree of correspondence between the obtained posture information and the posture information included in the reference information, a frequency of discrepancy between the obtained posture information and the posture information included in the reference information, or complexity of the exercise posture, and provide a feedback corresponding to the identified execution level.

8. The electronic apparatus as claimed in claim 1, wherein the processor is configured to:
   obtain a status information of the user based on the image obtained while the content is provided through the display;
   identify the execution status of the user associated with each of the plurality of steps by comparing the obtained status information and the status information included in the reference information; and
   control the display to provide the guide information corresponding to the step requiring feedback based on the execution status of the user, wherein the step is from among the plurality of steps.

9. The electronic apparatus as claimed in claim 8, wherein the processor is configured to:
obtain a first status information of the user by inputting the image to a first neural network model;
obtain a second status information of the user by inputting a voice of the user to a second neural network model; and
control the display to provide the guide information corresponding to the step requiring feedback based on the identified execution status, the first status information, and the second status information.

10. The electronic apparatus as claimed in claim 8, further comprising:
a speaker,
wherein the processor is configured to, based on the image of the user not being obtained while information associated with one step from among the plurality of steps is provided, control the speaker to output the guide information associated with the content.

11. A controlling method of an electronic apparatus, comprising:
obtaining an image photographing a user through a camera while a content that provides information is displayed, the content comprising information corresponding to a plurality of steps;
obtaining context information associated with the user based on the image;
identifying an execution status of the user associated with the information provided by the content by comparing the obtained context information and the reference information associated with the content;
controlling an output state of the content based on the execution status of the user; and
controlling a display to provide guide information corresponding to a step, requiring a feedback, from among the plurality of steps based on the identified execution status.

12. The method as claimed in claim 11, wherein the content includes respective sub information corresponding to each of a plurality of steps;
wherein the identifying the execution status of the user comprises, while the respective sub information corresponding to a first step from among the plurality of steps is provided through a display, identifying the execution status of the user associated with the first step by comparing the obtained context information and reference information corresponding to the respective sub information; and
wherein the controlling the output state of the content comprises controlling the output state of the content associated with the first step based on the execution status of the user.

13. The method as claimed in claim 12, wherein the identifying the execution status of the user comprises identifying an execution level corresponding to the execution status of the user; and
wherein the controlling the output state of the content comprises identifying information associated with a type of an output content corresponding to the identified execution level and controlling the output state of the content based on the type of the output content.

14. The method as claimed in claim 13, wherein the type of the output content includes at least one of a still image output, repeated output of sub information corresponding to a specific step, output speed adjustment, or enlarged output of contents.

15. The method as claimed in claim 11, wherein the obtaining context information associated with the user comprises obtaining posture information of the user based on the image obtained while the content that provides health information including an exercise posture is provided through a display; and
wherein the identifying the execution status of the user comprises:
identifying the execution status of the user associated with the exercise posture by comparing the obtained posture information of the user and posture information included in the reference information; and
providing a specific feedback for guiding the user's posture based on the execution status of the user.

16. The method as claimed in claim 15, wherein the electronic apparatus is implemented as a robot that provides a healthcare service; and
wherein the providing the specific feedback comprises:
performing an operation of correcting the user's posture or providing guide information for guiding the user's posture so that the user executes the exercise posture provided by the content based on the execution status of the user.

17. The method as claimed in claim 15, wherein the identifying the execution status of the user comprises:
identifying the execution level of the user based on at least one of a degree of correspondence between the obtained posture information and the posture information included in the reference information, a frequency of discrepancy between the obtained posture information and the posture information included in the reference information, or complexity of the exercise posture, and
wherein the providing the specific feedback comprises:
providing a feedback corresponding to the identified execution level.

18. The method as claimed in claim 11, wherein the obtaining context information associated with the user comprises:
obtaining a status information of the user based on the image obtained while the content is provided through a display;
wherein the identifying the execution status of the user comprises:
identifying the execution status of the user associated with each of the plurality of steps by comparing the obtained status information and the status information included in the reference information; and
providing the guide information corresponding to the step requiring feedback based on the execution status of the user, wherein the step is from among the plurality of steps.

19. The method as claimed in claim 18, wherein the obtaining the status information of the user comprises:
obtaining a first status information of the user by inputting the image to a first neural network model;
obtaining a second status information of the user by inputting a voice of the user to a second neural network model; and
wherein the providing the guide information comprises:
providing the guide information corresponding to the step requiring feedback based on the identified execution status, the first status information, and the second status information.

20. A non-transitory computer readable recording medium storing computer instructions that cause an electronic apparatus to perform an operation when executed by a processor of the electronic apparatus, wherein the operation comprises;
- obtaining an image photographing a user through a camera while a content that provides information is displayed, the content comprising information corresponding to a plurality of steps;
- obtaining context information associated with the user based on the image;
- identifying an execution status of the user associated with the information provided by the content by comparing the obtained context information and the reference information associated with the content;
- controlling an output state of the content based on the execution status of the user; and
- controlling a display to provide guide information corresponding to a step, requiring a feedback, from among the plurality of steps based on the identified execution status.

* * * * *